United States Patent [19]

Cohen

[11] 4,110,349

[45] Aug. 29, 1978

[54] TWO-STEP METHOD FOR THE ALKENYLATION OF MALEIC ANHYDRIDE AND RELATED COMPOUNDS

[75] Inventor: Jerome Martin Cohen, University Heights, Ohio

[73] Assignee: The Lubrizol Corporation, Wickliffe, Ohio

[21] Appl. No.: 695,234

[22] Filed: Jun. 11, 1976

[51] Int. Cl.$^2$ ............................................. C07D 307/60
[52] U.S. Cl. ................................ 260/346.74; 560/190; 260/533 N
[58] Field of Search ................. 260/346.8 R, 533 N, 260/346.74; 560/190

[56] References Cited

U.S. PATENT DOCUMENTS

| | | | |
|---|---|---|---|
| 3,231,587 | 1/1966 | Rense | 260/346.8 |
| 3,445,386 | 5/1969 | Otto et al. | 252/32.7 |
| 3,912,764 | 10/1975 | Palmer, Jr. | 260/346.8 R |

Primary Examiner—Henry R. Jiles
Assistant Examiner—Bernard Dentz
Attorney, Agent, or Firm—James W. Adams, Jr.; William H. Pittman

[57] ABSTRACT

Substituted carboxylic acids of the type prepared by the alkylation of maleic anhydride with an olefin polymer (e.g., polybutene) are prepared by a two-step method which is more economical and efficient than previously known methods. In the first step, the alkylating hydrocarbon is reacted with an unsaturated dicarboxylic acid or derivative thereof in an amount of the latter equal to about 30–90% by weight of the amount required to afford the desired product, optionally in the presence of a small amount of chlorine. In the second step, additional acid or derivative thereof is added and the reaction is continued in the presence of added chlorine.

8 Claims, No Drawings

TWO-STEP METHOD FOR THE ALKENYLATION OF MALEIC ANHYDRIDE AND RELATED COMPOUNDS

This invention relates to an improved process for the preparation of substituted carboxylic acids and their derivatives. More particularly, it relates to an improvement in the method for preparing such acids or derivatives by reacting (A) at least one alkylating hydrocarbon with (B) at least one of maleic acid, fumaric acid, itaconic acid, and anhydrides and esters of any of these acids, at least a part of the reaction taking place in the presence of chlorine, said improvement comprising:

(I) Reacting reagent A with an amount of reagent B equal to about 30–90% by weight of the amount required to afford the desired product, in the presence of about 0–0.4 mole of chlorine per mole of reagent B; and subsequently (II) Introducing additional reagent B sufficient to afford the desired product and continuing the reaction in the presence of added chlorine, the amount of said added chlorine being up to about 4 moles per mole of said additional reagent B.

The preparation of substituted carboxylic acids and their anhydrides and esters from such unsaturated acids or acid derivatives as maleic anhydride, fumaric acid or itaconic acid has been known for some time. The products are useful in many ways. For example, they serve as anti-rust agents in lubricants and fuels and as intermediates in the preparation of metal salts, esters and nitrogen-containing products which are useful as viscosity index improvers, dispersants and the like in lubricants and fuels. Other uses are also known to those skilled in the art.

The methods heretofore used for the preparation of the substituted carboxylic acids comprises alkylation of the unsaturated acid or acid derivatives with an aliphatic hydrocarbon or halogenated aliphatic hydrocarbon at a temperature above about 200° C. The hydrocarbon is typically an olefin polymer such as polypropene or polybutene, having a number average molecular weight above about 200. Particularly when the alkylating agent is a hydrocarbon, the reaction is frequently carried out in the presence of chlorine. In many instances, high temperatures and long reaction times are required. These facts, coupled with the necessity for the use of chlorine which is relatively dangerous to use, as well as being expensive and sometimes in short supply, make it desirable to develop alternative methods for the preparation of substituted carboxylic acids or derivatives, which methods are more economical in their use of chemicals and energy.

One such method has been described in U.S. Pat. No. 3,912,764. It comprises a two-stage process in which an olefin polymer is first caused to undergo a thermal reaction with maleic anhydride to a point short of conversion of all of said maleic anhydride, and subsequently an amount of chlorine less than one mole for each remaining mole of maleic anhydride is added and the reaction is continued in the presence of said chlorine. While this process is said to be more economical than those previously known since it uses a relatively small amount of chlorine and, to a large extent, can be carried out at relatively low temperatures, it is inefficient in that the product is described as containing on the order of 30% unreacted olefin polymer. This polymer is a useful petrochemical intermediate and the lack of a convenient method for its separation from the product results in waste since the unreacted polymer in the product serves no useful purpose.

A principal object of the present invention, therefore, is to produce an improved method for preparing substituted carboxylic acids and their derivatives.

A further object is to provide a method for alkylation of unsaturated dicarboxylic acids (or their derivatives) with olefin polymers and the like which requires a minimum of expensive chemicals and of expended energy.

A further object is to provide a method for producing substituted carboxylic acids or derivatives which is relatively efficient and convenient to carry out.

Other objects will in part be obvious and will in part appear hereinafter.

As noted hereinabove, the chemicals used in the method of this invention are (A) a suitable alkylating hydrocarbon; (B) maleic, fumaric or itaconic acid or an anhydride or ester thereof; and chlorine. If reagent B is an ester, it is preferably a lower alkyl ester, the work "lower" denoting radicals having up to 7 carbon atoms. Most often, reagent B is the free acid or the anhydride, and it is preferably maleic anhydride.

The alkylating hydrocarbon constituting reagent A is a substantially aliphatic hydrocarbon which contains one olefinic bond but is otherwise substantially saturated. By "substantially aliphatic" is meant hydrocarbons containing no more than 10% non-aliphatic (i.e., alicyclic or aromatic) carbon atoms. By "substantially saturated" is meant hydrocarbons containing no more than one olefinic or acetylenic carbon-carbon bond for every 10 carbon-carbon bonds in the molecule. Suitable hydrocarbons include olefinic petroleum fractions and olefin polymer, the latter being preferred. The invention will be described hereinafter principally with reference to olefin polymers.

The olefin polymers are usually those prepared by polymerization of lower olefins, i.e., olefins containing up to 7 carbon atoms. Polymers derived from both monoolefins and diolefins are within the scope of the invention. Suitable monoolefins include ethylene, propylene, 1-butene, 2-butene, isobutene and the pentenes, hexenes and heptenes (all isomers included). The diolefins may be conjugated or nonconjugated; suitable conjugated diolefins include butadienes, isoprene, 1,3-pentadiene and 1,3-hexadiene, and suitable nonconjugated diolefins include 1,4-pentadiene, 1,4-hexadiene and 1,5-hexadiene.

The preferred olefin polymers are those derived from monoolefins, especially mono-1-olefins and more especially $C_{2-6}$ mono-1-olefins such as ethylene, propylene and the butenes. Homopolymers and interpolymers are suitable, and the interpolymers may be ordinary chain interpolymers or graft interpolymers. The preferred polymers are homopolymers and interpolymers derived from mixtures of monomers differing in size by at most about two carbon atoms, such as ethylene-propylene interpolymers and the polybutenes more fully described hereinafter.

As previously noted, the olefin polymer can contain minor proportions of alicyclic or aromatic carbon atoms which may be derived from such monomers as cyclopentene, cyclohexene, methylene cyclopentene, methylene cyclohexene, 1,3-cyclohexadiene, norbornene, norbornadiene, cyclopentadiene, styrene and α-methylstyrene.

The olefin polymer usually contains about 30–300 and preferably about 50–250 carbon atoms. The number average molecular weight of the polymer, as determined by gel permeation chromatography, is ordinarily about 420–10,000, especially about 700–5,000 and more especially about 750–3,000.

A particularly preferred class of olefin polymers comprises the polybutenes, which are prepared by polymerization of one or more of 1-butene, 2-butene and isobutene. Especially desirable are polybutenes containing a substantial proportion of units derived from isobutene. The polybutene may contain minor amounts of butadiene which may or may not be incorporated in the polymer. Most often the isobutene units constitute 80%, preferably at least 90%, of the units in the polymer. These polybutenes are readily available commercial materials well known to those skilled in the art. Disclosures thereof will be found, for example, in U.S. Pat. Nos. 3,215,707; 3,231,587; 3,515,669; and 3,579,450, as well as in the aforementioned U.S. Pat. No. 3,912,764. The above are incorporated by reference for their disclosures of suitable polybutenes and also for their description of suitable diluents as disclosed hereinafter.

As will be apparent from the above description, mixtures of alkylating hydrocarbons can be used as reagent A. Polymers, in fact, are inherently such mixtures. It is also within the scope of the invention to use mixtures of polymers of different monomer combinations, such as a mixture of polybutene and polyethylene, a mixture of polybutene and an ethylene-propylene copolymer, or the like. Mixtures of acids, anhydrides and/or esters may also be used as reagent B; illustrative are maleic acid-fumaric acid mixtures, mixtures of methyl itaconate and methyl maleate, and mixtures of maleic acid and maleic anhydride. Most often, however, it is convenient and therefore desirable to use a single reagent as reagent B.

The molar ratio of reagent A to reagent B may vary according to the proportion of acid or acid derivative radicals desired in the product. Typically, about 0.3–2.0 moles of reagent B are used per mole of reagent A, but it is usually desirable to use at least one mole of reagent B per mole of reagent A so as to minimize the amount of unreacted olefin polymer present in the product.

In step I of the method of this invention, reagent A is reacted with an amount of reagent B equal to about 30–90% by weight of the amount required to afford the desired product, optionally in the presence of chlorine. The exact amount of reagent B used per mole of reagent A will, of course, depend on the total relative amounts of both reagents required to afford the desired product, as well as on the degree of completion desired to be achieved in the first step. Preferably, about 40–90% of the total amount of reagent B is employed in step I.

Step I may be carried out in the total absence of chlorine, or in the presence of an amount of chlorine up to about 0.4 mole per mole of reagent B used in this step. Most often, the amount of chlorine used will be less than about 0.1 mole per mole of reagent B. The exact order of addition of reagents is not critical, but it is usually convenient to prepare a mixture of reagents A and B and pass chlorine into that mixture as necessary to enable the reaction to proceed in the desired manner. The reaction temperature is usually on the order of 100°–250° C. and it is preferred that the temperature be at least about 150° C. during most of step I.

In step II of the method of this invention, additional reagent B is introduced as required to afford the desired product and the reaction is continued in the presence of added chlorine. The amount of added chlorine is usually at least about 0.9–4.0 moles, and generally about 0.9–2.0 moles, per mole of added reagent B. The reaction temperatures for step II are generally also within the range of about 100°–250° C. but are often somewhat higher than the temperature in step I, although higher temperatures are not always required. The preferred temperature range for step II is about 170°–225° C.

The point at which the reaction is essentially complete can be determined by analyzing the reaction mixture for the percentage of reagent B remaining and for the saponification number.

The method of this invention can be carried out in the presence of a substantially inert, normally liquid organic diluent such as a mineral oil of lubricating oil viscosity, a lower molecular weight hydrocarbon solvent such as benzene, toluene, xylene, petroleum naphtha, reformate, etc., although such diluents are most often unnecessary. When a volatile diluent is used, it is often preferable to carry out the reaction at pressures in excess of atmospheric, usually up to about 5 atmospheres. Generally, however, the reaction can be carried out at atmospheric pressure. Further details as to the diluents which can be used, as well as details as to reaction times and pressures, can be found in the U.S. patents cited hereinabove.

The method of this invention is illustrated by the following examples. All parts are by weight. Molecular weights are number average molecular weights determined by gel permeation chromatography.

EXAMPLE 1

One part of chlorine is introduced underneath the surface of a mixture of 135 parts (1.38 moles) of maleic anhydride and 1171 parts (1.17 moles) of a polybutene containing predominantly isobutene units and having a molecular weight of 750–1100. The reaction mixture is initially at 93° C. and is heated to 201°–207° C. and maintained within that range for 4 hours, after which 30 parts of additional chlorine is added at 201°–207° C. over 5.2 hours. The total chlorine added during this first step is 0.44 mole.

An additional 35 parts (0.36 mole) of maleic anhydride is added and the mixture is chlorinated with an additional 28 parts (0.39 mole) of chlorine at 201°–207° C. for 4 hours. The product is the desired polybutenyl-substituted succinic anhydride having a saponification number of 104 and a viscosity (100° C.) of 3515 SUS.

EXAMPLE 2

One part (0.014 mole) of chlorine is introduced under the surface of 1161 parts (1.17 moles) of the polybutene of Example 1 at 98° C. Maleic anhydride, 54 parts (0.55 mole) is then added and the mixture is heated for 4 hours at 186°–190° C.

An additional 81 parts (0.83 mole) of maleic anhydride and 70 parts of chlorine are added over 5.2 hours at 177°–189° C. Heating at this temperature is continued for 1.4 hours, after which an additional 9 parts of chlorine is added over 0.8 hour. Heating is continued for two hours and 3 more parts of chlorine are added over 0.3 hour; the total chlorine added in the second stage of the reaction is 1.16 moles. The product is the desired polybutenyl succinic anhydride having a saponification number of 104 and a viscosity at 99° C. of 4322 SUS.

EXAMPLE 3

As described in Example 2, 1161 parts (1.16 moles) of the polybutene of Example 1 is treated with 1 part of chlorine gas and 64 parts (0.65 mole) of maleic anhydride is added. The mixture is heated to 196° C. over 10.7 hours.

An additional 38 parts (0.39 mole) of maleic anhydride is added and the mixture is heated at 190°–193° C. for 3 hours. An additional 32 parts (0.33 mole) of maleic anhydride is then added and 68 parts (0.96 mole) of chlorine is passed in at 189°–194° C. over 10.7 hours. The product is the desired polybutenyl-substituted succinic anhydride having a saponification number of 100 and a viscosity at 99° C. of 4311 SUS.

EXAMPLE 4

A mixture of 6400 parts (4 moles) of a polybutene comprising predominantly isobutene units and having a molecular weight of about 1600 and 408 parts (4.16 moles) of maleic anhydride is heated at 225°–240° C. for 4 hours. It is then cooled to 170° C. and an additional 102 parts (1.04 moles) of maleic anhydride is added, followed by 70 parts (0.99 mole) of chlorine; the latter is added over 3 hours at 170°–215° C. The mixture is heated for an additional 3 hours at 215° C. and is then vacuum stripped at 220° C. and filtered through diatomaceous earth. The product is the desired polybutenyl-substituted succinic anhydride having a saponification number of 61.8.

EXAMPLE 5

Maleic anhydride, 133 parts (1.36 moles), is reacted with 3000 parts (3.0 moles) of the polybutene of Example 1 for 1.75 hours at 195° C. Additional maleic anhydride, 205 parts (2.09 moles), is then added followed by 208 parts (2.9 moles) of chlorine; the latter is added at 200°–205° C. over 4.5 hours. The resulting product is vacuum stripped at 215° C. and filtered through diatomaceous earth to yield the desired polybutenyl-substituted succinic anhydride having a saponification number of 62.4.

The above examples are summarized as regards molar quantities, ratios and the like in the following table. For each of steps I and II, mole ratios are based on amounts of reagent B and chlorine added during that step only. As will be apparent from the table, the method of this invention is economical with respect to the use of chlorine, substantially less than one mole thereof being required per mole of reagent B.

What is claimed is:

1. In a method for preparing a substituted carboxylic acid or derivative thereof which comprises reacting (A) at least one substantially aliphatic hydrocarbon having about 30–300 carbon atoms and containing on olefinic bond but being otherwise substantially saturated with (B) about 0.3–2.0 moles, per mole of reagent A, of at least one of maleic acid, fumaric acid, itaconic acid, and anhydrides and esters of any of these acids, at least a part of the reaction taking place in the presence of chlorine, the improvement which comprises:
   (I) Reacting reagent A with an amount of reagent B equal to about 30–90% of the amount required to afford the desired product, at a temperature within the range of about 100°–250° C. and in the presence of about 0–0.4 mole of chlorine per mole of reagent B; and subsequently
   (II) Introducing additional reagent B sufficient to afford the desired product and continuing the reaction at a temperature within the range of about 170°–225° C. and in the presence of about 0.9–4 moles of added chlorine per mole of said additional reagent B;
   the total amount of chlorine used in said method being substantially less than one mole per mole of reagent B.

2. A method according to claim 1 wherein reagent A is an olefin polymer.

3. A method according to claim 2 wherein reagent B is maleic anhydride.

4. A method according to claim 3 wherein reagent A is a polybutene having a number average molecular weight in the range of about 750–3000, and wherein the product has an acid number or saponification number, as determined by ASTM method D3339 or D94, of at least about 60.

5. A method according to claim 4 wherein chlorine is present during step I and is used in an amount up to about 0.1 mole per mole of reagent B.

6. A method according to claim 5 wherein about 40–90% by weight of the total amount of maleic anhydride is added in step I.

7. A method according to claim 4 wherein no chlorine is used in step I.

8. A method according to claim 7 wherein at least about 40% by weight of the total amount of maleic anhydride is added in step I.

|         |       | Moles      |            |          | % (wt.)    | Mole ratio          |                     |
|---------|-------|------------|------------|----------|------------|---------------------|---------------------|
| Example | Step  | Reagent A  | Reagent B  | Chlorine | Reagent B  | Reagent B/Reagent A | Chlorine/Reagent B  |
| 1       | I     | 1.17       | 1.38       | 0.44     | 68         | 1.18                | 0.32                |
|         | II    | —          | 0.36       | 0.39     | 32         | 0.31                | 1.08                |
|         | Total | 1.17       | 1.74       | 0.83     |            | 1.49                | 0.48                |
| 2       | I     | 1.17       | 0.55       | 0.014    | 34         | 0.47                | 0.025               |
|         | II    | —          | 0.83       | 1.16     | 66         | 0.71                | 1.40                |
|         | Total | 1.17       | 1.38       | 1.17     |            | 1.18                | 0.85                |
| 3       | I     | 1.16       | 0.65       | 0.014    | 41         | 0.56                | 0.022               |
|         | II    | —          | 0.72       | 0.96     | 59         | 0.63                | 1.33                |
|         | Total | 1.16       | 1.37       | 0.97     |            | 1.19                | 0.71                |
| 4       | I     | 4.0        | 4.16       | 0        | 80         | 1.04                | 0                   |
|         | II    | —          | 1.04       | 0.99     | 20         | 0.26                | 0.95                |
|         | Total | 4.0        | 5.20       | 0.99     |            | 1.30                | 0.19                |
| 5       | I     | 3.0        | 1.36       | 0        | 39         | 0.45                | 0                   |
|         | II    | —          | 2.09       | 2.9      | 61         | 0.71                | 1.39                |
|         | Total | 3.0        | 3.45       | 2.9      |            | 1.16                | 0.84                |

* * * * *